(12) United States Patent
Janna et al.

(10) Patent No.: US 11,315,714 B2
(45) Date of Patent: Apr. 26, 2022

(54) ACTUATION SYSTEM AND METHOD FOR ORTHOPEDIC IMPLANTS WITH A ROTATABLE INTERNAL MAGNET

(71) Applicant: Smith & Nephew, Inc., Memphis, TN (US)

(72) Inventors: Sied W. Janna, Memphis, TN (US); Robert Hill, London (GB)

(73) Assignee: Smith & Nephew, Inc., Memphis, TN (US)

( * ) Notice: Subject to any disclaimer, the term of this patent is extended or adjusted under 35 U.S.C. 154(b) by 532 days.

(21) Appl. No.: 16/473,942

(22) PCT Filed: Dec. 26, 2017

(86) PCT No.: PCT/US2017/068394
§ 371 (c)(1),
(2) Date: Jun. 26, 2019

(87) PCT Pub. No.: WO2018/125856
PCT Pub. Date: Jul. 5, 2018

(65) Prior Publication Data
US 2019/0326043 A1    Oct. 24, 2019

Related U.S. Application Data

(60) Provisional application No. 62/440,486, filed on Dec. 30, 2016.

(51) Int. Cl.
*H01F 7/02* (2006.01)
*A61B 17/72* (2006.01)
*A61B 17/00* (2006.01)

(52) U.S. Cl.
CPC ....... *H01F 7/0242* (2013.01); *A61B 17/7216* (2013.01); *H01F 7/0273* (2013.01);
(Continued)

(58) Field of Classification Search
CPC .......... H01F 7/02–7/04; A61B 17/7216; A61B 2017/02411; A61F 2250/0001
See application file for complete search history.

(56) References Cited

U.S. PATENT DOCUMENTS

| 4,810,987 A | 3/1989 | Liebthal et al. |
| 2008/0218298 A1 | 9/2008 | Miyata |

(Continued)

OTHER PUBLICATIONS

International Search Report and Written Opinion for International Application No. PCT/US2017/068394, dated Apr. 26, 2018, 8 pages.

(Continued)

*Primary Examiner* — Ramon M Barrera
(74) *Attorney, Agent, or Firm* — Kacvinsky Daisak Bluni PLLC

(57) ABSTRACT

An external magnetic actuator for use in adjusting an implantable medical device having a magnetically actuatable rotatable portion, such as an intramedullary (EVI) lengthening nail is disclosed. The actuator may include a magnet having opposite major surfaces representing opposite poles of the magnet. The magnet may be contained within an actuator body having first and second handles coupled to first and second opposing side walls of the housing. The actuator body may also include one or more projections operable to prevent first and/or second walls of the actuator body from lying flat against an external planar surface. Also provided are various kits and systems that include a disclosed external magnetic actuator and methods for using the disclosed external magnetic actuator.

11 Claims, 5 Drawing Sheets

(52) U.S. Cl.
CPC ............... *A61B 2017/00411* (2013.01); *A61F 2250/0001* (2013.01); *H01F 7/02* (2013.01)

(56) References Cited

U.S. PATENT DOCUMENTS

2011/0230883 A1    9/2011   Zahrly et al.
2012/0005868 A1    1/2012   Suderman

OTHER PUBLICATIONS

International Preliminary Report on Patentability for International application No. PCT/US2017/068394, dated Jul. 11, 2019, 6 pages.

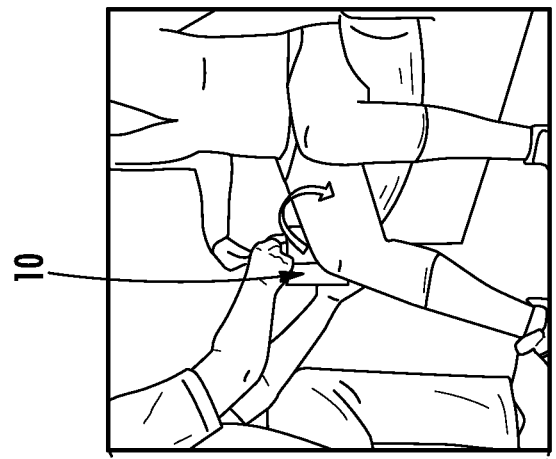
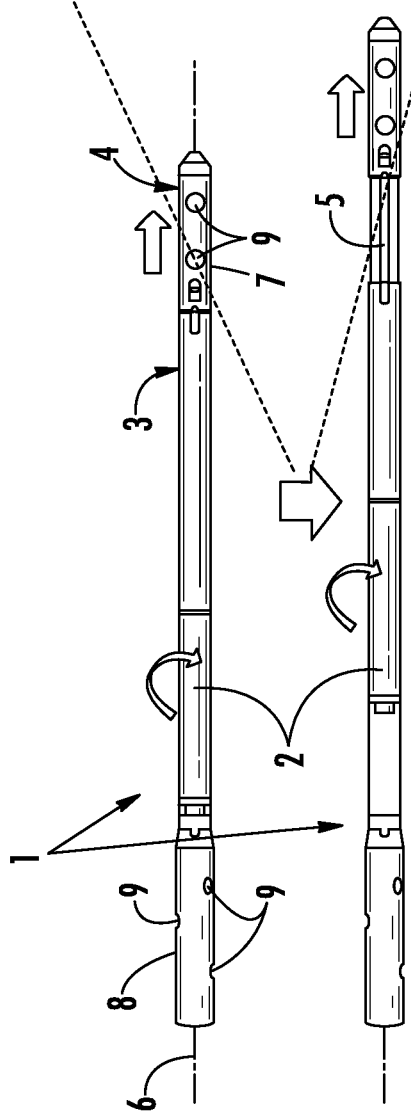
FIG. 1B
FIG. 1A

ACTUATION SYSTEM AND METHOD FOR ORTHOPEDIC IMPLANTS WITH A ROTATABLE INTERNAL MAGNET

CROSS-REFERENCE TO RELATED APPLICATIONS

This application is a United States National Phase filing of International Application No. PCT/US2017/068394, filed Dec. 26, 2017, which claims priority to U.S. Provisional Patent Application Ser. No. 62/440,486, entitled "Actuation System and Method for Orthopedic Implants with a Rotatable Internal Magnet", filed Dec. 30, 2016, the entirety of each application is hereby incorporated by reference herein.

TECHNICAL FIELD

The present disclosure generally relates to actuation devices and systems for actuating implantable bone adjustment devices, and more particularly, relates to actuation devices and systems for actuating implantable bone adjustment devices that include internal rotatable magnets that operate as drivers for axial displacement of different components of the device, such as, for example and without limitation, magnetically actuatable limb-lengthening intramedullary nails or magnetically actuatable intramedullary bone transport nails.

BACKGROUND

Implantable bone adjustment devices are occasionally used in orthopedic procedures to gradually adjust the position, orientation, geometry and/or length of a bone or to promote bone growth across a gap, such as a gap resulting from surgical resection of a portion of a long bone. One form of such a bone adjustment device is a limb-lengthening nail (LLN) that is implanted in the medullary canal of a long bone and subsequently manipulated to adjust the length of the bone. One currently-available LLN is a telescoping nail that includes an internal magnet that is connected to a threaded rod. Rotating the magnet rotates the threaded rod and lengthens or shortens the telescoping nail. An external actuator is applied to the limb to rotate the internal magnet by applying a rotating magnetic field. To apply sufficient torque to rotate the internal magnet against resistive forces, certain prior art devices use two permanent driving magnets positioned such that the south pole of one is facing the north pole of the other, and such that the part of the patient's body that surrounds the implanted LLN is positioned between the two permanent magnets. One such actuator that has been described includes two magnets that are rotated by a motorized system while they are held against the limb at the level of the internal magnet in the implanted LLN.

In systems that utilize a magnetic coupling to manipulate the implant, the ability of the system to distract the bone against the forces of the bone callus and soft tissue is directly related to the strength of the magnetic coupling between the internal magnet of the implant and the magnet in the external actuation unit, as well as the resistive friction forces internal to the device. For patients with a large limb diameter, the distance between the nail and actuator reduces the coupling strength due to the greater distance between the internal magnet and the external magnets. Accordingly, certain conventional magnetically-actuated implant systems are contraindicated for patients with a large limb diameter.

A variety of challenges arise in the provision of a rotating magnetic field of sufficient strength to rotate an internal magnet of an implanted medical device, including, for example, safe handling, use and transport of a large magnet having sufficient strength to reliably couple with an implanted internal magnet and provide sufficient torque to rotate the internal magnet. Therefore, a need remains for further improvements in this technological field. The present disclosure addresses this need.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides devices, kits, systems and methods for actuating an implanted or implantable medical device.

There is provided an external magnetic actuator for actuating an implanted or implantable medical device that includes a rotatable internal magnet for driving translation between first and second components of the implanted or implantable medical device, the external magnetic actuator comprising a permanent magnet having a first major surface, a second major surface opposite the first major surface, and a plurality of minor surfaces extending between and perpendicular to the first and second major surfaces, the first and second major surfaces each having an individual surface area, the plurality of minor surfaces each having an individual surface area, the individual surface area of the first and second major surfaces being greater than the individual surface area of each of the minor surfaces, the permanent magnet including a first pole on the first major surface, and a second pole on the second major surface; an actuator body including a housing having a first wall, a second wall opposite the first wall, a plurality of side walls extending between and perpendicular to the first and second walls, and a cavity for receiving the permanent magnet therein; a first handle coupled to a first side wall of the plurality of side walls; and a second handle coupled to a second side wall of the plurality of side walls, the second side wall being opposite to the first side wall.

In some embodiments, the first handle may include a first end and a second end, the first handle being coupled to the first side wall at the first end of the first handle, the second end of the first handle being uncoupled from the first side wall.

In some embodiments, the second handle may include a first end and a second end, the second handle being coupled to the second side wall at the first end of the second handle, the second end of the second handle being uncoupled from the second side wall.

In some embodiments, the first and second handles may extend generally parallel to the first and second side walls, respectively.

In some embodiment, the first handle may be spaced a first distance from the first side wall and the second handle may be spaced a second distance from the second side wall, the first and second distances being sufficient to allow a user's fingers to fit between the first handle and the first side wall, and the second handle and the second side wall.

In some embodiments, the second wall may be a panel that is coupled to the housing via one or more fasteners.

In some embodiments, the external magnetic actuator may further comprise an adhesive for sealing the panel to the plurality of side walls such that the permanent magnet is hermetically sealed within the actuator body.

In some embodiments, the first and second sets of projections may be operable to prevent the first and second walls, respectively, from lying flat against an external surface.

In some embodiments, the first set of projections may include a plurality of projections defining a first distal edge extending beyond a first plane defined by an outside surface of the first wall, and the second set of projections may include a plurality of projections defining a second distal edge extending beyond a second plane defined by an outside surface of the second wall.

In some embodiments, the first set of projections may extend from the first and second side walls beyond the first wall, and the second set of projections may extend from the first and second side walls beyond the second wall.

There is provided a kit comprising an external magnetic actuator according to any of the preceding claims; and a transport container for storing the external magnetic actuator; wherein the transport container is operable to contain a magnetic field generated by the permanent magnet of the external magnetic actuator such that a second magnetic field immediately adjacent to the transport container is no greater than 5 milli-Gauss at a distance of 2.1 meters.

There is a provided a method of rotating a magnetic rotatable portion of an implantable medical device including first and second bodies, a threaded rod operably coupled to the first and second bodies, and a rotatable internal magnet operably associated with the threaded rod so that rotation of the internal magnet drives rotation of the threaded rod and movement of the first body with respect to the second body, the method comprising providing an external magnet having a first major surface, a second major surface opposite the first major surface, and a plurality of minor surfaces extending between and perpendicular to the first and second major surfaces, the first and second major surfaces each having an individual surface area, the plurality of minor surfaces each having an individual surface area, the individual surface area of the first and second major surfaces being greater than the individual surface area of each of the minor surfaces, the permanent magnet including a first pole on the first major surface, and a second pole on the second major surface; placing the first pole of the external magnet at a first position adjacent to a portion of the rotatable internal magnet to magnetically couple the external magnet with the rotatable internal magnet, the rotatable internal magnet having an opposite polarity from the first pole of the external magnet, the first position of the external magnet comprising an initial location relative to the implantable medical device; moving the external magnet from the initial location to a destination location via moving the external magnet in an arc of about 180 degrees in a rotatable direction of the rotatable internal magnet while maintaining the first pole of the external magnet substantially equidistant from, and oriented toward, the implantable medical device to rotate the rotatable internal magnet about 180 degrees; magnetically uncoupling the external magnet from the rotatable internal magnet by increasing a distance between the external magnet and the rotatable internal magnet without substantially moving the external magnet in a rotatable direction of the rotatable internal magnet; moving the external magnet to the initial location; placing the second pole of the external magnet adjacent to a portion of the rotatable internal magnet to magnetically recouple the external magnet with the rotatable internal magnet in a second orientation; and moving the external magnet from the initial location to the destination location via moving the external magnet in an arc of about 180 degrees in the rotatable direction of the rotatable internal magnet while maintaining the second pole of the external magnet substantially equidistant from, and oriented toward, the implantable medical device to rotate the rotatable internal magnet about 180 degrees.

In some embodiments, the method may further comprise uncoupling the external magnet from the rotatable internal magnet by increasing a distance between the external magnet and the rotatable internal magnet without substantially moving the external magnet in a rotatable direction of the rotatable internal magnet; moving the external magnet to the initial location; placing the first pole of the external magnet adjacent to a portion of the rotatable internal magnet to magnetically recouple the external magnet with the rotatable internal magnet in the first orientation; and moving the external magnet from the initial location to the destination location via moving the external magnet in an arc of about 180 degrees in the rotatable direction of the rotatable internal magnet while maintaining the first pole of the external magnet substantially equidistant from, and oriented toward, the implantable medical device to rotate the rotatable internal magnet about 180 degrees.

In some embodiments, rotating the rotatable internal magnet of the implantable medical device in a first rotational direction may translate a portion of the implantable medical device in a first linear direction, and rotating the rotatable internal magnet of the implantable medical device in a second rotational direction opposite from the first rotational direction may translate a portion of the implantable medical device in a second linear direction opposite from the first linear direction.

Embodiments of the present invention provide numerous advantages. For example, ease of handling and manipulation by a user, facilitating transport of the device, strength to withstand an accidental drop, and water resistance to allow for easy cleaning. In addition, use of an external magnetic actuator according to some of the embodiments of the present invention, allow for easier use to manipulate internal rotatable magnets in either direction with no modifications of the external magnetic actuator required. Use of the external magnetic actuator also enables faster operation, readily achieving a desired amount of rotation to an internal rotatable magnet for a single session within a fraction of the time required by other known actuators. This shortened treatment time is advantageous for multiple reasons, including, for example, reduction in the time spent in an operating room environment during a surgical procedure distracting an implantable lengthening device intraoperatively, thus minimizing costs and time spent by the patient under anesthesia. In the case of postoperative uses, it also reduces patient use time.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

FIG. 1A illustrates a side view of an example embodiment of an intramedullary nail having an adjustable length;

FIG. 1B illustrates a perspective view of an example embodiment of an external magnetic actuator used in connection with the intramedullary nail shown in FIG. 1A;

Figure 2:
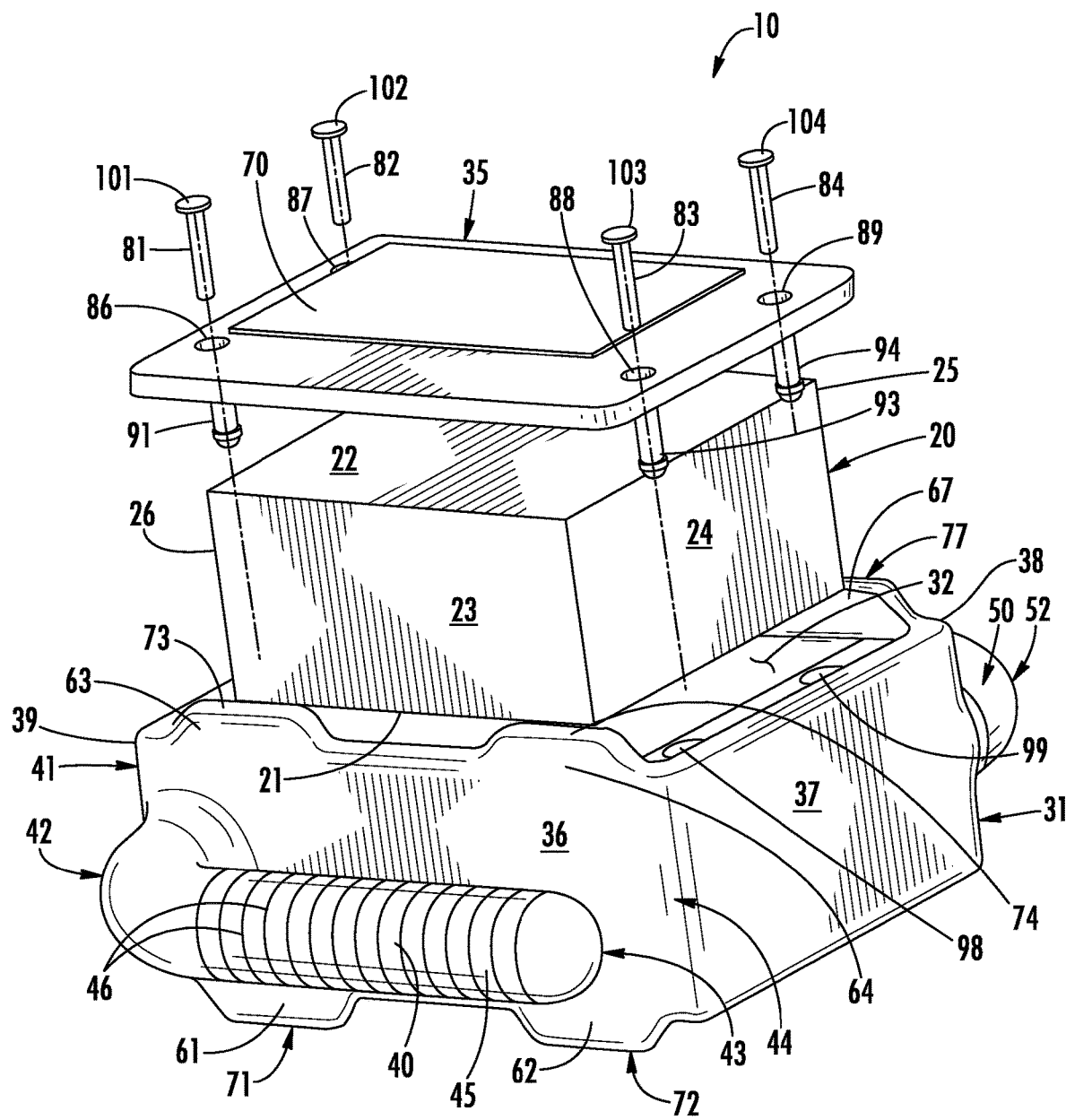
FIG. 2 illustrates an exploded perspective view of the external magnetic actuator shown in FIG. 1B.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be further understood that this disclosure is not limited to the illustrated embodiments.

DETAILED DESCRIPTION

For the purposes of promoting an understanding of the principles of the invention, reference will now be made to the embodiments illustrated in the figures and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring to FIGS. 1B-3, an example embodiment of an external magnetic actuator 10 is illustrated. The external magnetic actuator 10 is configured for use in adjusting an implantable medical device having a magnetically actuatable rotatable portion, such as an intramedullary (IM) lengthening nail 1. The external magnetic actuator 10 may include a permanent magnet 20 and an actuator body 30 configured to contain the permanent magnet 20. For purposes of this disclosure, the permanent magnet 20 is hereafter referred to herein as an "external magnet 20" to more clearly distinguish the external magnet 20 positioned within the external magnetic actuator 10 from a magnet positioned within the implantable medical device, such as magnet 2 positioned within the IM lengthening nail 1 (FIG. 1A), which is referred to herein as an "internal magnet".

Figures 4A, 4B:
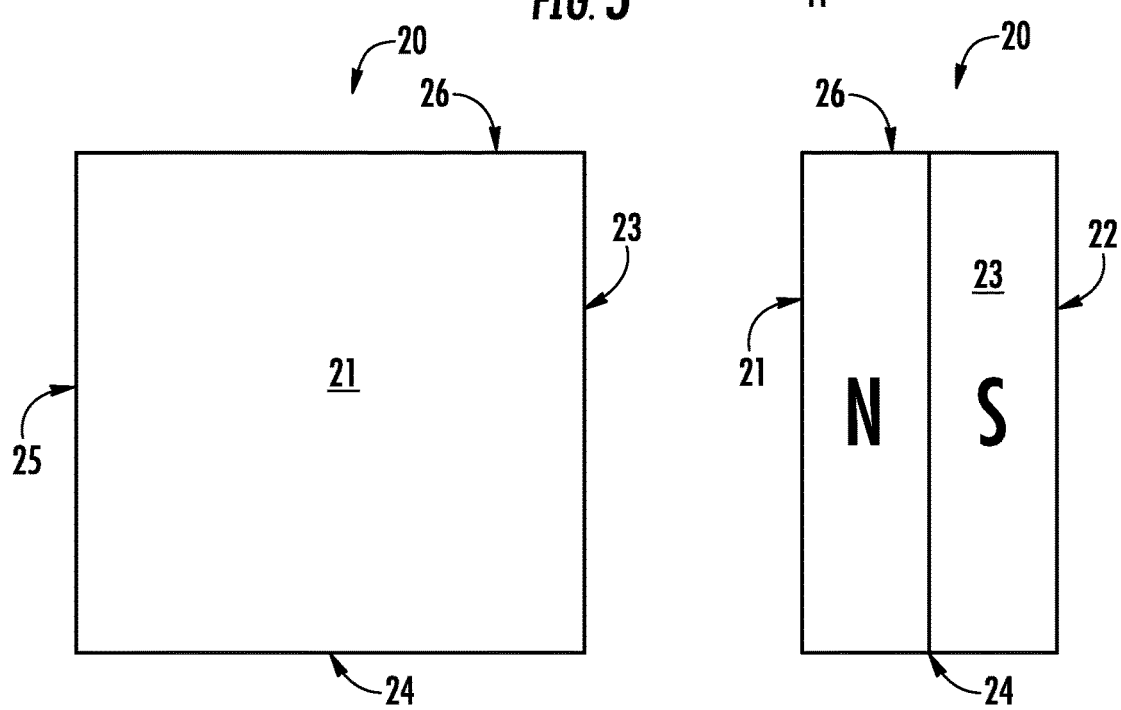
FIG. 4A is a top plan view of an example embodiment of a permanent magnet that may be used with the external magnetic actuator shown in FIG. 2.
FIG. 4B is a side view of the permanent magnet shown in FIG. 4A.

Referring to FIGS. 2, 4A and 4B, the external magnet 20 may include a generally planar first major surface 21, a generally planar second major surface 22 opposite to and generally parallel to the first major surface 21, and a plurality of generally planar minor surfaces or side surfaces 23, 24, 25, 26 extending between the first and second major surfaces 21, 22 and generally perpendicular to the first and second major surfaces 21, 22. As such, the external magnet 20 may have the shape of a square or rectangle, although it is envisioned that the external magnet may be provided in other shapes. Referring to FIGS. 4A and 4B, in one embodiment, the polarization of the external magnet 20 may bisect the external magnet 20 generally parallel to the first and second major surfaces 21, 22 such that first major surface 21 represents a first pole and the second major surface 22 represents a second pole.

Figure 3:
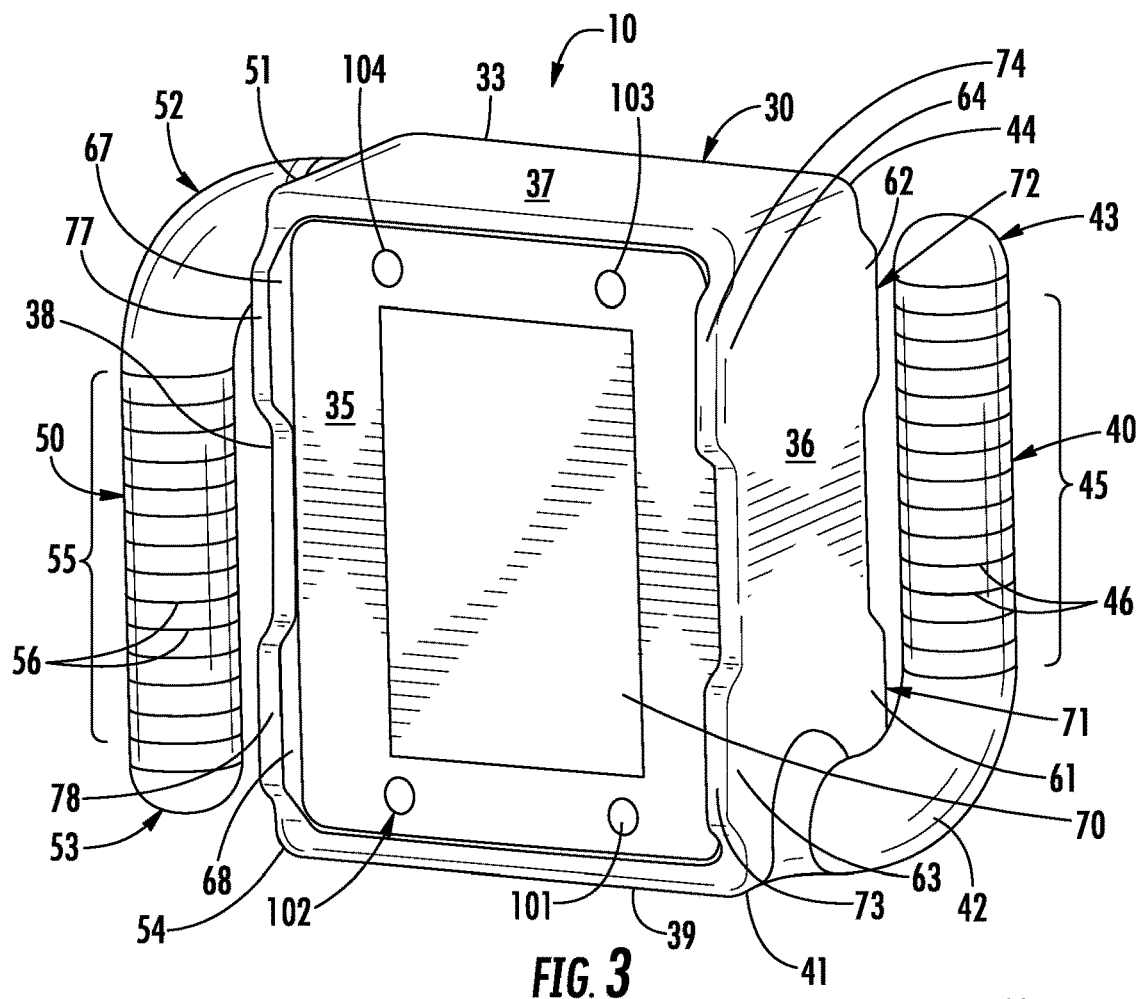
FIG. 3 illustrates a perspective view of the assembled external magnetic actuator embodiment shown in FIG. 2.

Referring to FIGS. 2 and 3, the actuator body 30 may be configured to contain the external magnet 20. That is, the actuator body 30 may include a housing 31 that defines a cavity 32 for receiving the external magnet 20 therein. In the embodiment shown, the housing 31 may be machined from a block of polymeric material such that the dimensions of the cavity 32 closely conforms to the dimensions of the external magnet 20. However, it is envisioned that the housing can be manufactured from any suitable material in any suitable manner as now known or hereafter developed.

As illustrated, when assembled, the housing 31 may include a first wall 33 positioned adjacent the first major surface 21 of the external magnet 20. The actuator body 30 may also include a panel 35 that is formed separately from the housing 31. In use, the panel 35 may be coupled, attached, affixed, engaged, etc. (used interchangeably herein without the intent to limit) to the housing 31 during assembly of the external magnetic actuator 10 (e.g., the panel 35 may be coupled to the housing 31 after the external magnet 20 has been positioned within the cavity 32 to completely cover or seal the external magnet 20 within the actuator body 30). The panel 35 may be positioned adjacent the second major surface 22 of the external magnet 20. The housing 31 may also include a plurality of minor walls or side walls 36, 37, 38, 39. Each one of minor walls 36, 37, 38, 39 may be positioned adjacent one of minor surfaces 23, 24, 25, 26 of the external magnet 20. As such, the housing 31 may have the shape of a square or rectangle similar to the external magnet 20, although it is envisioned that the housing may be provided in other shapes.

Minor wall 36 may be generally parallel to the minor wall 38 positioned on the opposite side of the external magnet 20, while minor wall 37 may be generally parallel to the minor wall 39 positioned on the opposite side of the external magnet 20. In one embodiment, the thicknesses of the first wall 33, the panel 35, and the minor or side walls 36, 37, 38, 39 are selected to provide an optimized balance of strength needed to resist fracture of the housing 31 in the event that the external magnetic actuator 10 is dropped, while also remaining sufficiently thin to minimize the distance between the external magnet 20 and the implant device such as, for example, the IM lengthening nail 1. In one embodiment, a warning label 70 may be placed on the outside surface of the panel 35.

Referring to FIGS. 2 and 3, the external magnetic actuator 10 may also include a first handle 40 coupled to minor wall 36 and a second handle 50 coupled to the opposite minor wall 38. In use, incorporation of the first and second handles 40, 50 permit a user to hold and manipulate the external magnetic actuator 10. More particularly, the first handle 40 may be coupled to a first edge 41 of the minor wall 36 at only a first end 42 of the first handle 40, while a second end 43 of the first handle 40 remains uncoupled to the minor wall 36. The first handle 40 may extend in a direction toward a second edge 44 of the minor wall 36, as such, the first handle 40 may extend generally parallel with the minor wall 36 and spaced apart from the minor wall 36. Similarly, the second handle 50 may be coupled to a first edge 51 of the opposite minor wall 38 at only a first end 52 of the second handle 50, while the second end 53 of the second handle 50 remains uncoupled to the minor wall 38. The second handle 50 may extend in a direction toward a second edge 54 of the minor wall 38 in a similar manner as described above in connection with the first handle 40, as such, the second handle 50 may extend generally parallel with the minor wall 38 and spaced apart from the minor wall 38.

In the embodiment shown, each of first and second handles 40, 50 may include a generally cylindrical grip portion 45, 55. As illustrated, outer surfaces of the grip portions 45, 55 may include a plurality of ribs 46, 56 to provide for an improved grip by a patient or a medical care provider during use of the external magnetic actuator 10. In addition, or alternatively, each of the first and second handles 40, 50 may include soft grip portions that may be, for example, slidably positioned over the first and second handles 40, 50. The grip portions may be provided to improve patient comfort when handling the external magnetic actuator 10. In one embodiment, each of the grip portions 45, 55 of each of the first and second handles 40, 50 has a diameter that is determined based on a set of anthropomorphic data. In one preferred embodiment, the first and second diameters are no greater than a fifth percentile female hand length based on the anthropomorphic data.

The grip portions 45, 55 of each of the handles 40, 50 may be spaced apart a predetermined distance from the respective minor wall 36, 38, respectively, to which it is attached to provide for clearance between the grip portion 45, 55 and the minor walls 36, 38, respectively, to which it is attached to accommodate the fingers of a patient or medical care provider gripping the first and second handles 40, 50 during use of the external magnetic actuator 10. In one embodiment, the grip portions 45, 55 of each of the first and second handles 40, 50 may be spaced from its respective minor wall 36, 38 a predetermined distance, referred to herein as a "first distance" for the first handle 40 and a "second distance" for the second handle 50. The first and second distances may be determined based on a set of anthropomorphic data. In one preferred embodiment, each of the first and second distances is at least as great as a ninety-fifth percentile male finger width based on the anthropomorphic data.

In the embodiment shown in FIGS. 2 and 3, the minor wall 36, 38 may also include projections 61, 62, 63, 64, 67, 68 and two similar projections not shown. Using an outside surface of the first wall 33, which is generally planar, as a first frame of reference, projections 61, 62 of minor wall 36 and the projections (not shown) of minor wall 38 extend beyond the outside surface of the first wall 33 and therefore are operable to prevent the first wall 33 from lying flat against a separate planar surface. Similarly, using an outside surface of panel 35, which is generally planar, as a second frame of reference, projections 63, 64 of minor wall 36 and projections 67, 68 of minor wall 38 extend beyond the outside surface of panel 35 and therefore are operable to prevent panel 35 from lying flat against a separate planar surface. Projections 61, 62, 63, 64, 67, 68 and the two projections not shown help distance the external magnet 20 from any external metal surfaces, such as, for example refrigerator doors, filing cabinets, etc., to which the external magnet 20 may be drawn if the external magnetic actuator 10 is inadvertently brought into close proximity therewith. While the external magnetic actuator 10 has been illustrated and described as incorporating eight projections, one skilled in the art will appreciate that that external magnetic actuator may include any number of projections including more or less projections.

Distal edges 71, 72 of projections 61, 62, and the distal edges of the two projections not shown may lie on an opposite side of a plane defined by the outside surface of the first wall 33 from the external magnet 20. Distal edges 73, 74, 77, 78 of projections 63, 64, 67, 68 may lie on an opposite side of a plane defined by the outside surface of panel 35 from the external magnet 20. In one embodiment, the distal edges 71, 72 and the distal edges of the two projections not shown lie generally in a first plane that is spaced apart from the outside surface of the first wall 33, and the distal edges 73, 74, 77, 78 lie generally in a second plane that is spaced apart from the outside surface of the panel 35. In another embodiment of the external magnetic actuator 10, the first handle 40 may be positioned such that it is spaced apart from the first plane a third distance and spaced apart from the second plane a fourth distance, the second handle 50 may be positioned such that it is spaced apart from the first plane a fifth distance and spaced apart from the second plane a sixth distance, and each of the third, fourth, fifth and sixth distances may be determined based on a set of anthropomorphic data. In one preferred embodiment, each of the third, fourth, fifth and sixth distances is at least as great as a ninety-fifth percentile male finger width based on the anthropomorphic data. This positioning of the first and second handles 40, 50 has the advantage of preventing fingers from being pinched between the first and second handles 40, 50 and the external surface to which the external magnetic actuator 10 may be attracted if it is inadvertently brought too close to such a surface, such as, for example, a side of a refrigerator, filing cabinet, or other surface composed of ferritic materials.

In one embodiment, the housing 31 and the first and second handles 40, 50 may be formed as a single unitary component, although it is envisioned that the housing and first and second handles may be formed as separate components and then coupled together. In the illustrated embodiment, the housing 31 and the first and second handles 40, 50 may be manufactured from a plastic material. For example, in the embodiment shown, the housing 31 and the first and second handles 40, 50 may be machined from a single polymeric work piece. It should be understood however that the housing and the first and second handles may be manufactured from any suitable material now known or hereafter developed.

Referring to FIG. 2, to assemble the external magnetic actuator 10, the external magnet 20 may be positioned in the cavity 32 of the housing 31. In one embodiment, the first major surface 21 of the external magnet 20 may be positioned adjacent to the first wall 33 of the housing 31, minor surface 23 of the external magnet 20 may be positioned adjacent to the minor wall 36, minor surface 24 of the external magnet 20 may be positioned adjacent to the minor wall 37, minor surface 25 of the external magnet 20 may be positioned adjacent to the minor wall 38, and minor surface 26 of the external magnet 20 may be positioned adjacent to the minor wall 39. One of ordinary skill in the art will appreciate that this is one possible configuration of many, and that the external magnet 20 may be positioned within the cavity 32 of the housing 31 in other alignments and configurations.

The second major surface 22 of the external magnet 20 may be, at this stage of assembly, still exposed. The panel 35 may then be positioned adjacent the second major surface 22 and affixed to the housing 31. In a preferred embodiment, the panel 35 may be sealingly engaged to the housing 31 such that the external magnet 20 is hermetically sealed within the actuator body 30. Sealing engagement of the panel 35 to the housing 31 enables external magnetic actuator 10 to be thoroughly cleaned in its assembled state for a subsequent use or for use with a different patient. In the embodiment shown, the panel 35 is attached to the housing 31 using smooth headed push pins 81, 82, 83, 84, which are inserted through apertures 86, 87, 88, 89 formed in the panel 35 and into bulbed receivers 91, 93, 94 (and one similar bulbed received not shown) that are positioned within cavities 98, 99 (and two similar cavities not shown) formed in the housing 31. Once the push pins 81, 82, 83, 84 are in place following attachment of the panel 35 to the housing 31, their smooth heads 101, 102, 103, 104 may align with the outer surface of the panel 35 to form a generally smooth surface. One of ordinary skill in the art will appreciate that the panel 35 may be coupled to the housing 31 by any means now known or hereafter developed including, without limitation, fasteners, nails, adhesive, etc. In addition, while it has been illustrated and described as the panel corresponds to second wall, it will be appreciated that the panel may be any of the walls of the housing.

The housing 31 and the panel 35 preferably are rigid and relatively thin walled, at least in the portions directly covering the major surfaces 21, 22 of the external magnet 20 in order to minimize the gap between the external magnet 20 and an internal rotatable magnet, such as internal magnet 2, of an implantable medical device, such as, for example, IM lengthening nail 1.

In one embodiment, prior to coupling the panel 35 with the housing 31, an adhesive can be applied to the portions of the housing 31 that contact panel 35 such that affixation of the panel 35 to the housing 31 by insertion of, for example, push pins 81, 82, 83, 84, hermetically seals the external magnet 20 within the actuator body 30. A wide variety of adhesives can be used for this purpose. In one embodiment, the adhesive may be a hydrophobic adhesive. In another embodiment, the adhesive may be a two-part epoxy that cures to form a water tight seal between the panel 35 and the housing 31. In another embodiment, the adhesive may be Loctite M-121HP Hysol adhesive. An advantage of using an adhesive to make the external magnetic actuator 10 water tight is that doing so enables the external magnetic actuator 10 to be submerged in an aqueous liquid for cleaning and sterilization. More particularly, a water tight seal prevents water from entering the cavity 32 and also prevents patient contaminants, such as for example, blood borne pathogens that may contact the external magnetic actuator 10 during use, from entering the cavity 32, which facilitates cleaning of the external magnet actuator 10 as it is reprocessed for use with another patient. In this regard, once a prescribed treatment for a given patient in completed, the external magnetic actuator 10 can be returned to its manufacturer or to another service provider for reprocessing and subsequent use by another patient. Reprocessing requires thorough cleaning and sterilization, which is facilitated by the design of the external magnetic actuator 10 and, in particular, by the use of a water tight adhesive.

Generally speaking, in use, the external magnetic actuator 10 may be used to position and manipulate the external magnet 20 near an implanted device having, for example, a rotatable portion that is coupled to a rotatable internal magnet to apply torque to the inner magnet of the implanted device and thereby rotate the rotatable portion, all the while, the external magnet 20 is positioned external to the patient. In a typical device of this type, the internal rotatable magnet may include a generally cylindrical shape. In addition, the internal rotatable magnet may be diametrically magnetized (e.g., poles are perpendicular to the longitudinal axis of the internal magnet). In the presence of a magnetic driving field perpendicular to the rotational axis of the internal magnet and rotating around this axis, the internal magnet tends to become oriented in the magnetic driving field, which applies a torque to the internal magnet and causes the internal magnet to rotate in the rotational direction of the magnetic driving field, if the applied torque is greater than the load torque of the rotatable portion of the implanted medical device under the load applied to it at the time when the magnetic driving field is activated. Rotation of the rotatable portion of the implanted medical device displaces at least one component relative to another component of the device.

In use, the external magnetic actuator 10 provides sufficient torque to rotate the internal magnet despite the distance between the internal magnet and the external magnet 20 and applied forces on the rotatable portion of the implanted medical device. In this regard, the torque applied to the internal magnet by the external magnetic actuator 10 must overcome any compressive load imparted on the rotatable portion of the implanted medical device by bone tissue and other tissues of the patient. Thus, by operating the external magnetic actuator 10 as described herein, a desired displacement of one component relative to another component may be achieved.

In one, non-limiting, embodiment, the implanted medical device can be an intramedullary limb lengthening nail such as IM lengthening nail 1 depicted in FIG. 1A. Further details regarding a representative IM lengthening nail are available in U.S. Pat. No. 8,777,947, which is hereby incorporated herein by reference in its entirety. Generally, the IM lengthening nail 1 may include a first body 3, a second body 4, and a rotatable threaded rod 5 that engages at least one component affixed to first body 3 and at least one component affixed to second body 4. The IM lengthening nail 1 may also include an internal magnet 2 coupled to the threaded rod 5 such that rotation of the internal magnet 2 drives rotation of the threaded rod 5. This can be achieved, for example, by fixing the threaded rod 5 directly to the internal magnet 2 or a casing in which the internal magnet 2 is contained, or can be achieved by connecting the threaded rod 5 indirectly to the internal magnet 2, such as through a gear mechanism positioned therebetween.

The first and second bodies 3, 4 are dimensioned such that the first and second bodies 3, 4 are able to move in at least one axial direction with respect to one another upon rotation of the threaded rod 5. Typically, at least one of the first and second bodies 3, 4 encompasses or houses the internal magnet 2. As described in further detail below, the internal magnet 2 may be rotated about a longitudinal axis 6 of IM lengthening nail 1 by the external magnetic actuator 10. The IM lengthening nail 1 may also include a first locking portion 7 and a second locking portion 8, each of which includes a plurality of fastener openings 9 structured to receive fasteners for coupling the respective ends of the IM lengthening nail 1 to the patient's bone. The internal magnet 2 typically includes at least one permanent magnet, one of the poles of which is directed in one radial direction relative to the longitudinal axis 6 and the other pole directed in an opposite radial direction relative to the longitudinal axis 6.

To rotate the rotatable portion of an implanted medical device, such as, for example, the threaded rod 5 of the IM lengthening nail 1, that is coupled to a rotatable internal magnet such as, for example, internal magnet 2 of the IM lengthening nail 1, the external magnet 20 of the external magnetic actuator 10 may be magnetically coupled with the rotatable internal magnet 2 in a first orientation by placing the first pole of the external magnet 20 of the external magnetic actuator 10 at a first position adjacent to a portion of the rotatable internal magnet 2 having an opposite polarity from the first pole of the external magnet 20. This first position of the external magnetic actuator 10 is referred to herein as the initial location of the external magnetic actuator 10 relative to the implantable medical device. The external magnetic actuator 10 is then moved from the initial location generally in an arc of about 180 degrees in a rotatable direction of the rotatable internal magnet while maintaining the first pole of the external magnet 20 substantially equidistant from, and oriented toward, the implantable medical device to rotate the rotatable internal magnet about 180 degrees. In a preferred embodiment, the arc through which the external magnetic actuator 10 moves may be an arc traversing the front of a patient's limb. This second position of the external magnetic actuator 10 being referred to as a destination location relative to the implantable medical device. The external magnet 20 of the external magnetic actuator 10 may then be uncoupled from the rotatable internal magnet by increasing the distance between the external magnet 20 of the external magnetic actuator 10 and the rotatable internal magnet of the implantable medical device (e.g., internal magnet 2 of the IM lengthening nail 1) without substantially moving the external magnet 20 of the external magnetic actuator 10 in a rotatable direction of the magnetic rotatable portion. In one embodiment, rotating the rotatable internal magnet of the implantable medical device in a first rotational direction translates a portion of the implantable medical device in a first linear direction. In another embodiment, rotating the rotatable internal magnet of the implantable medical device in a second rotational direction opposite from the first rotational direction translates a portion of the implantable medical device in a second linear direction opposite from the first linear direction.

If further rotation of the rotatable internal magnet of the implanted medical device is desired, the external magnet 20, while the external magnetic actuator 10 and the rotatable internal magnet are uncoupled, may be returned to the initial location, but with the second pole of the external magnet 20 oriented toward the implantable medical device to magnetically recouple the external magnet 20 of the external magnetic actuator 10 with the rotatable internal magnet in a second orientation. The external magnetic actuator 10 may then be moved from the initial location generally in an arc of about 180 degrees to the destination location in a rotatable direction of the rotatable internal magnet while maintaining the second pole of the external magnet 20 substantially equidistant from, and oriented toward, the implantable medical device to rotate the rotatable internal magnet about 180 degrees.

Further rotation of the rotatable internal magnet of the implanted medical device (e.g., internal magnet 2 of the IM lengthening nail 1) can be achieved until a desired adjustment of the implantable medical device is reached. Additional rotation of the internal magnet of the implanted medical device can be achieved by repeating the acts of (i) uncoupling the external magnet 20 of the external magnetic actuator 10 from the rotatable internal magnet by increasing the distance between the external magnet 20 and the rotatable internal magnet without substantially moving the external magnet 20 in a rotatable direction of the magnetic rotatable portion; (ii) while the external magnetic actuator and the rotatable internal magnet are uncoupled, returning the external magnet 20 to the initial location; and (iii) moving the external magnet 20 generally in an arc of about 180 degrees to the destination location in a rotatable direction of the rotatable internal magnet while maintaining the respective first or second pole of the external magnet 20 substantially equidistant from, and oriented toward, the implantable medical device to rotate the rotatable internal magnet about 180 degrees. Each time the external magnet 20 is returned to the initial location, its orientation relative to the rotatable internal magnet is alternated between the first and second orientations. To this end, the opposite walls of the housing 31 may be color coded with different colors (e.g., black and white, etc.) to inform, remind, etc. patients and care givers to rotate the external magnet 20 on successive rotations.

As will be appreciated, the ability of external magnetic actuator 10 to rotate the internal magnet 2 to lengthen IM lengthening nail 1, or lengthen or otherwise displace components of another implanted device relative to one another, against the forces of the bone callus and soft tissue is determined in part by the strength of the magnetic coupling between the internal magnet 2 and the external magnet 20. For patients with a large limb diameter, the distance between the internal magnet 2 and the external magnet 20 reduces the strength of the magnetic coupling, which reduces the amount of torque applied to the internal magnet 2 by the external magnetic actuator 10. The ability of the external magnetic actuator 20 to rotate the rotatable internal magnet also depends in part upon the resistive frictional forces internal to the implanted device, such as friction between engaged threads of different components within the device.

To maximize the operable coupling distance between the external magnetic actuator 10 and the internal magnet of the implanted medical device and to optimize the torque placed on the internal magnet by movement of the external magnetic actuator 10 in an arc as described above, the external magnet 20 preferably is a relatively strong permanent magnet. In one embodiment, the external magnet 20 may be a Neodymium N-50 or Neodymium N-52 rare earth magnet. In one embodiment, each of first and second major surfaces 21, 22 of the external magnet 20 has a surface area of about 16 square inches and each of the minor surfaces 23, 24, 25, 26 has a surface area of about 8 square inches. In one embodiment, the external magnet 20 is in the shape of a rectangular cuboid having dimensions of about 4 inches by 4 inches by 2 inches.

A wide variety of options exist for producing external magnetic actuator embodiments having modified features relative to those shown and described herein or having different combinations of the disclosed features. For example, it is possible to provide external magnetic actuators having different dimensions and/or different shapes without departing from the disclosure. In addition, the external magnet 20 can be substituted with multiple smaller magnets in cavity 32.

Various external magnetic actuator embodiments disclosed herein have one or more desirable features, including one or more of ease of handling and manipulation by a user, strength to withstand an accidental drop, and water resistance to allow for easy cleaning. External magnetic actuator embodiments also can be easily used to drive internal rotatable magnets in either directions, according to requirements, with no modifications of the external magnetic actuator required. Use of external magnetic actuator embodiments according to this disclosure also is faster than other known actuators, readily achieving a desired amount of rotation to an internal rotatable magnet for a single session within a fraction of the time required by other known actuators. This shortened treatment time is advantageous for multiple reasons, including, for example, that it reduces the time spent in an operating room environment during a surgical procedure distracting an implantable lengthening device intraoperatively, thus minimizing costs and time spent by the patient under anesthesia. In the case of postoperative uses, it also reduces patient use time.

Figure 5:
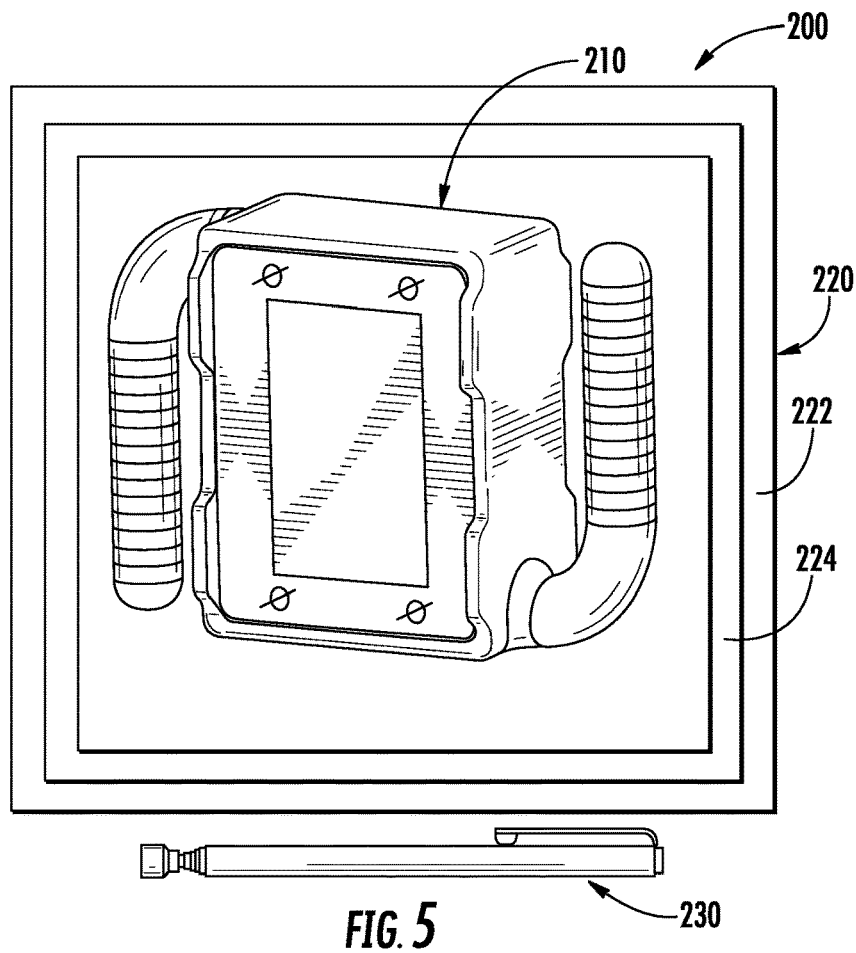
FIG. 5 is a schematic representation of a kit in accordance with one embodiment of the disclosure.

As will be appreciated by a person of ordinary skill in the art, a magnet such as those described above produces a relatively strong magnetic field. While this feature is advantageous in terms of maximizing the operable coupling distance between the external magnetic actuator 10 and the internal magnet of the implanted medical device and optimizing the torque placed on the internal magnet by movement of the external magnetic actuator 10 in an arc, it also presents other challenges that are addressed by the present disclosure. For example, to satisfy various regulatory requirements, shipment of the external magnetic actuator 10 requires containment of the external magnetic actuator 10 in a container that significantly reduces the magnetic field emanated from the container. Moreover, reduction of the magnetic field emanating from the container is also important to prevent undesirable effects on other devices that may come into close proximity to the container, such as, for example, communications devices, pacemakers, credit cards utilizing magnetic strips to encode information, etc. Therefore, referring to FIG. 5, the present disclosure provides a kit 200 that includes an external magnetic actuator 210, such as external magnetic actuator 10, and a transport container 220 for the external magnetic actuator 210. In one embodiment, the transport container 220 includes a plastic body 222 and an internal lining 224 to block a first magnetic field produced by the external magnetic actuator 210 such that a second magnetic field immediately adjacent to the transport container 220 is no greater than 5 milli-Gauss at a distance of 2.1 meters. In one embodiment, the internal lining 224 is formed from sheet metal having a thickness of at least 1 mm, although it is envisioned that the internal lining may be any suitable material now known or hereafter developed.

Another challenge that arises when transporting or using a device that produces such a strong magnetic field is that the device tends to attract other materials, such as, for example, ferritic materials, and devices that include components made from such materials. For example, if external magnetic actuator 210 is removed from the transport container 220 in close proximity to a refrigerator, a filing cabinet, etc., the external magnetic actuator 210 may be forcefully pulled into contact therewith and become attached to a surface thereof. While projections 61, 62, 63, 64, 67, 68 formed on the external magnetic actuator 210 help to distance the external magnet 20 from such surfaces to facilitate separation of the external magnetic actuator 210 from such surfaces, it is preferred to verify that a given location is a magnet safe environment before removing the external magnetic actuator 210 from the transport container 220. To address this issue, with continued reference to FIG. 5, the kit 200 may also include a scout magnet 230 that can be used to sweep the area where limb lengthening will occur to check for magnetic materials prior to removing the external magnetic actuator 210 from the transport container 220. In one embodiment, the scout magnet 230 is operable to produce a magnetic field having a field strength of about 300 to about 3000 Gauss at the surface of the magnet. By moving the scout magnet 230 around the immediate area surrounding the place where the external magnetic actuator 210 will be used (such as, for example, a 4-5-foot radius), this area can be checked for magnetic (e.g., ferritic) materials and define a "magnet safe zone" for patient use.

Figure 7:
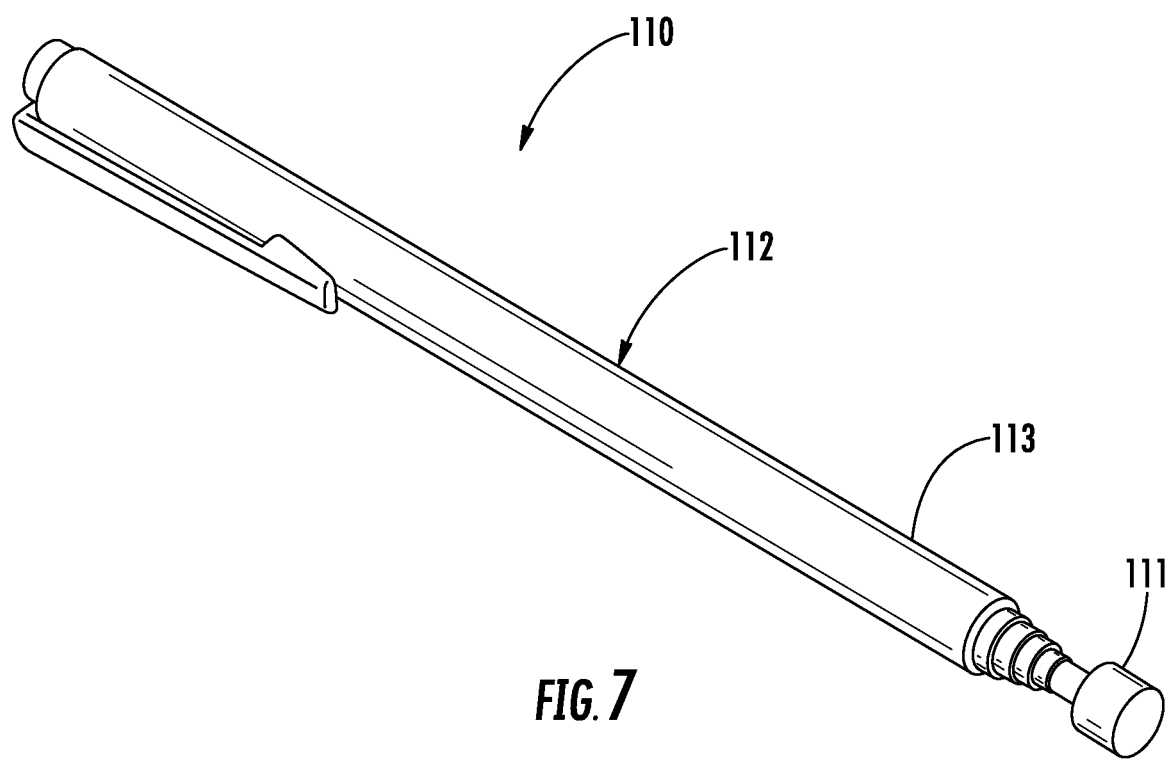
FIG. 7 is a perspective view of a scout magnet device in accordance with one embodiment of the disclosure.

In another embodiment, the scout magnet 230 is in the form of a scout magnet device 110, as shown in FIG. 7, in which a small magnet 111 is affixed to a scout magnet body 112, which may be, for example a telescoping body operable to be extended to increase the distance between the small magnet 111 and a grip portion of the scout magnet body 112. Telescoping shaft 113 can be, for example, one that is extendable approximately 25 inches. Use of a scout magnet on a telescoping shaft facilitates verification that an area is a magnet safe zone. The scout magnet 111 can be used to sweep an area surrounding the transport container 220 before removing the external magnetic actuator 210 from the transport container 220, thereby providing a mechanism to identify any magnetic materials for possible removal thereof from the vicinity of the transport container 220 before removing the external magnetic actuator 210 from the transport container 220 or to inform the user of the external magnetic actuator 210 of nearby structures to be avoided during use of the external magnetic actuator 210.

Figure 6:
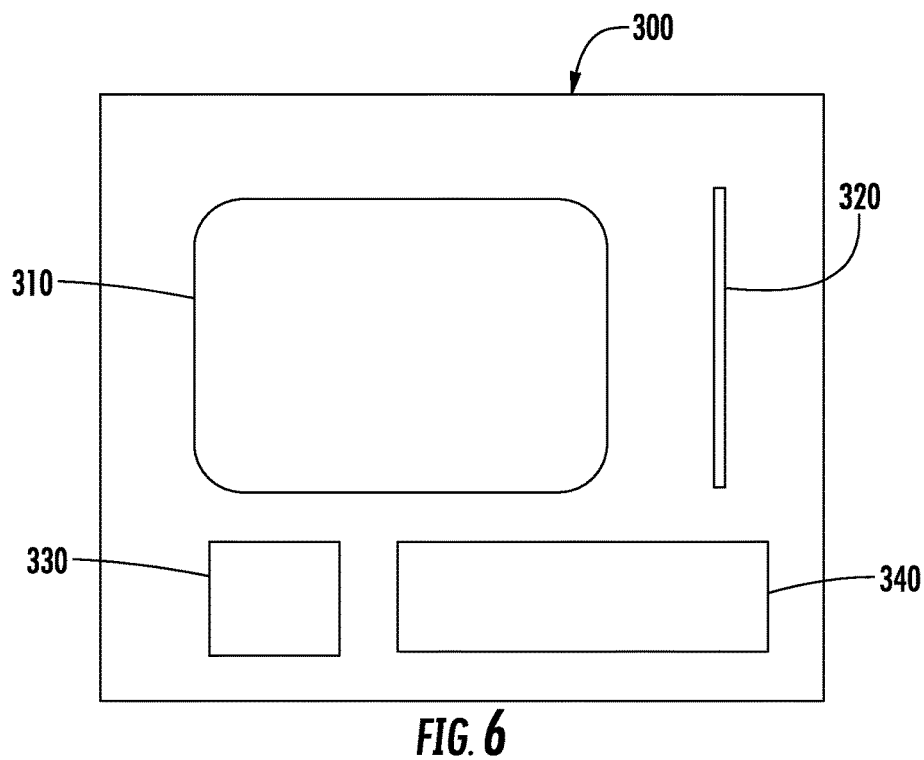
FIG. 6 is a schematic representation of a system in accordance with one embodiment of the disclosure.

Referring to FIG. 6, in there is provided a system 300 that includes an external magnetic actuator 310, such as external magnetic actuator 10, and at least one implantable medical device 320 having a rotatable internal magnet such as, for example, IM lengthening nail 1. The system 300 may further include a plurality of bone screws 330 to affix the implantable medical device 320 to one or more bones or bone fragments. The system 300 may further include instrumentation 340 for aligning and/or driving bone screws 330.

As will be appreciated from the descriptions herein and the associated Figures, a wide variety of embodiments are contemplated by the present disclosure, examples of which include, without limitation, the following:

In one embodiment, there is provided an external magnetic actuator for use in adjusting an implantable medical device having a magnetic rotatable portion for driving translation between components of the implantable medical device. The external magnetic actuator includes a permanent magnet and an actuator body configured to contain the permanent magnet. The permanent magnet has a generally planar first major surface, a generally planar second major surface opposite to and generally parallel to the first major surface, and a plurality of generally planar minor surfaces extending between the first and second major surfaces and generally perpendicular to the first and second major surfaces. The first and second major surfaces each having a greater surface area than each of the plurality of minor surfaces. The permanent magnet's polarization may bisect the permanent magnet generally parallel to the first and second major surfaces such that the first major surface represents a first pole and the second major surface represents a second pole. The actuator body may include (i) a housing defining a cavity for containing the permanent magnet, the housing including a first wall positioned adjacent the first major surface of the permanent magnet and a plurality of minor walls, each one of the minor walls positioned adjacent one of the minor surfaces of the permanent magnet, wherein the plurality of minor walls includes at least first and second minor walls that are generally parallel to one another and positioned on opposite sides of the permanent magnet; (ii) a panel configured to be affixed to the housing to form a second wall positioned adjacent the second major surface of the permanent magnet; (iii) a first handle coupled to the first minor wall; and (iv) a second handle coupled to the second minor wall. In one embodiment, the actuator body is a sealed container.

In another embodiment of the external magnetic actuator, the housing may include a plurality of projections operable, in use, to prevent the actuator body (e.g., first and second major surfaces) from lying flat against a planar surface (e.g., an external, metal planar surface) that the external magnetic actuator may come into contact with during use. In one embodiment, two projections extend in opposite directions from each of two opposite side walls as extensions of the side walls and generally coplanar therewith, thereby providing four projections extending beyond the outside surface of the first major wall and four protections extending beyond the outside surface of the second major wall.

In another embodiment, the actuator body may include a first projection or a first set of projections defining a distal edge positioned on an opposite side of a plane defined by the outside surface of the first wall from the permanent magnet, the first projection or first set of projections being operable to prevent the first wall from lying flat against an external, metal planar surface. The actuator body may also include a second projection or a second set of projections defining a distal edge positioned on an opposite side of a plane defined by the outside surface of the second wall from the permanent magnet, the second projection or second set of projections being operable to prevent the second wall from lying flat against an external, metal planar surface. In one form of this embodiment, the projections may extend from the minor walls. In another embodiment, the first set of projections may include first and second projections, each of the first and second projections having a distal edge positioned on an opposite side of a plane defined by the outside surface of the first wall from the permanent magnet, the first and second projections being operable to prevent the first wall from lying flat against the external, metal planar surface, and the second set of projections may include third and fourth projections, each of the third and fourth projections having a distal edge positioned on an opposite side of a plane defined by the outside surface of the second wall from the permanent magnet, the third and fourth projections being operable to prevent the second wall from lying flat against the external, metal planar surface. In yet another embodiment, the first set of projections may include a first projection, a second projection, a third projection and a fourth projection, each of the first, second, third and fourth projections having a distal edge positioned on an opposite side of a plane defined by the outside surface of the first wall from the permanent magnet, the first, second, third and fourth projections being operable to prevent the first wall from lying flat against the external, metal planar surface, and the second set of projections may include a fifth projection, a sixth projection, a seventh projection and an eighth projection, each of the fifth, sixth, seventh and eighth projections having a distal edge positioned on an opposite side of a plane defined by the outside surface of the second wall from the permanent magnet, the fifth, sixth, seventh and eighth projections being operable to prevent the second wall from lying flat against the external, metal planar surface. In another form of this embodiment, the distal edges of the first, second, third and fourth projections lie substantially in a first plane, the distal edges of the fifth, sixth, seventh and eighth projections lie substantially in a second plane, the first handle is positioned such that the first handle is spaced apart from the first plane a first distance and spaced apart from the second plane a second distance, the second handle is positioned such that the second handle is spaced apart from the first plane a third distance and spaced apart from the second plane a fourth distance and each of the first, second, third and fourth distances is determined based on a set of anthropomorphic data such that the first, second, third and fourth distances are at least as great as a ninety-fifth percentile male finger width based on the anthropomorphic data.

In other embodiments, the handles are sized and/or positioned to create spaces of predetermined dimensions between the handles and other surfaces of the external magnetic actuator and/or between the handles and surfaces of other objects to which the external magnetic actuator may be attracted. In some embodiments, the dimensions of these spaces are determined based on a set of anthropomorphic data. In yet other embodiments, a hydrophobic adhesive is used to provide a water tight seal between the panel and the housing. The inclusion of projections and/or handle spacing features and/or water tight sealing in various embodiments facilitates safe and convenient handling and use of the external magnetic actuator embodiments.

In another embodiment of the external magnetic actuator, the first handle is coupled to the first minor wall at only one of the ends of the first handle. In yet another embodiment, the second handle is coupled to the second minor wall at only one of the ends of the second handle. In still another embodiment, the first handle has a first diameter, the second handle has a second diameter and the first and second diameters are determined based on a set of anthropomorphic data such that the first and second diameters are no greater than a fifth percentile female hand length based on the anthropomorphic data. In still yet another embodiment, the first handle is spaced from the first minor wall a first distance, the second handle is spaced from the second minor wall a second distance and the first and second distances are determined based on a set of anthropomorphic data such that the first and second distances are at least as great as a ninety-fifth percentile male finger width based on the anthropomorphic data.

In another embodiment of the present disclosure, there is provided a kit comprising an external magnetic actuator in accordance with any one of the embodiments disclosed herein and a transport container for the external magnetic actuator. The transport container is operable to contain a magnetic field generated by the permanent magnet of the external magnetic actuator so that the external magnetic actuator embodiments can be shipped or otherwise transported safely and within applicable regulatory guidelines. In one embodiment, the transport container includes a plastic body and an internal lining to block a first magnetic field produced by the external magnetic actuator such that a second magnetic field immediately adjacent the transport container is no greater than 5 milli-Gauss at a distance of 2.1 meters. In yet another embodiment, the internal lining comprises sheet metal having a thickness of at least 1 mm. In still another embodiment, the kit also includes a scout magnet. In one embodiment, the scout magnet may be used to ensure that a given area is a "magnet safe zone" prior to removal of the external magnetic actuator from the transport container.

Another embodiment of the disclosure is a system that includes an external magnetic actuator in accordance with any one of the embodiments disclosed herein and at least one implantable medical device having a rotatable internal magnet. In one embodiment, the system further includes a plurality of bone screws to affix the implantable medical device to one or more bones or bone fragments. In yet another embodiment, the system further includes instrumentation for aligning and driving bone screws.

In another embodiment, the present disclosure provides a method of rotating a rotatable portion of an implantable medical device that is coupled to a rotatable internal magnet having a rotational axis corresponding to a longitudinal axis of the implantable medical device. The method includes (i) providing an external magnetic actuator in accordance with any one of the embodiments disclosed herein; (ii) magnetically coupling the permanent magnet of the external magnetic actuator with the rotatable internal magnet in a first orientation by placing the first pole of the permanent magnet of the external magnetic actuator at a first position adjacent to a portion of the rotatable internal magnet having an opposite polarity from the first pole of the permanent magnet, the first position of the external magnetic actuator comprising an initial location relative to the implantable medical device; (iii) moving the external magnetic actuator from the initial location generally in an arc of about 180 degrees in a rotatable direction of the rotatable internal magnet while maintaining the first pole of the permanent magnet substantially equidistant from, and oriented toward, the implantable medical device to rotate the rotatable internal magnet about 180 degrees, this second position of the external magnetic actuator being referred to as a destination location relative to the implantable medical device; (iv) uncoupling the permanent magnet of the external magnetic actuator from the rotatable internal magnet by increasing the distance between the permanent magnet and the rotatable internal magnet without substantially moving the permanent magnet in a rotatable direction of the magnetic rotatable portion; (v) while the external magnetic actuator and the rotatable internal magnet are uncoupled, returning the permanent magnet to the initial location, but with the second pole of the permanent magnet oriented toward the implantable medical device to magnetically recouple the permanent magnet of the external magnetic actuator with the rotatable internal magnet in a second orientation; and (vi) moving the external magnetic actuator from the initial location generally in an arc of about 180 degrees to the destination location in a rotatable direction of the rotatable internal magnet while maintaining the second pole of the permanent magnet substantially equidistant from, and oriented toward, the implantable medical device to rotate the rotatable internal magnet about 180 degrees. In one embodiment, rotating the rotatable internal magnet of the implantable medical device in a first rotational direction translates a portion of the implantable medical device in a first linear direction. In another embodiment, rotating the rotatable internal magnet of the implantable medical device in a second rotational direction opposite from the first rotational direction translates a portion of the implantable medical device in a second linear direction opposite from the first linear direction.

In another embodiment, the method further includes repeating, until a desired adjustment of the implantable medical device is reached, the acts of: (i) uncoupling the permanent magnet of the external magnetic actuator from the rotatable internal magnet by increasing the distance between the permanent magnet and the rotatable internal magnet without substantially moving the permanent magnet in a rotatable direction of the magnetic rotatable portion; (ii) while the external magnetic actuator and the rotatable internal magnet are uncoupled, returning the permanent magnet to the initial location; and (iii) moving the external magnet generally in an arc of about 180 degrees to the destination location in a rotatable direction of the rotatable internal magnet while maintaining the respective first or second pole of the permanent magnet substantially equidistant from, and oriented toward, the implantable medical device to rotate the rotatable internal magnet about 180 degrees; wherein, each time the permanent magnet is returned to the initial location, its orientation relative to the rotatable internal magnet is alternated between the first and second orientations.

While the invention has been illustrated and described in detail in the drawings and foregoing description, the same is to be considered as illustrative and not restrictive in character, it being understood that only the preferred embodiments have been shown and described and that all changes, alternatives, modifications and equivalents that come within the spirit of the inventions are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. An external magnetic actuator for actuating an implanted or implantable medical device that includes a rotatable internal magnet for driving translation between first and second components of the implanted or implantable medical device, the external magnetic actuator comprising:

a permanent magnet having a first major surface, a second major surface opposite the first major surface, and a plurality of minor surfaces extending between and perpendicular to the first and second major surfaces, the first and second major surfaces each having an individual surface area, the plurality of minor surfaces each having an individual surface area, the individual surface area of the first and second major surfaces being greater than the individual surface area of each of the minor surfaces, the permanent magnet including a first pole on the first major surface, and a second pole on the second major surface;

an actuator body including a housing having a first wall, a second wall opposite the first wall, a plurality of side walls extending between and perpendicular to the first and second walls, and a cavity for receiving the permanent magnet therein;

a first handle coupled to a first side wall of the plurality of side walls; and a second handle coupled to a second side wall of the plurality of side walls, the second side wall being opposite to the first side wall.

2. The external magnetic actuator of claim 1, wherein the first handle includes a first end and a second end, the first handle being coupled to the first side wall at the first end of the first handle, the second end of the first handle being uncoupled from the first side wall.

3. The external magnetic actuator of claim 2, wherein the second handle includes a first end and a second end, the second handle being coupled to the second side wall at the first end of the second handle, the second end of the second handle being uncoupled from the second side wall.

4. The external magnetic actuator of claim 3, wherein the first and second handles extend generally parallel to the first and second side walls, respectively.

5. The external magnetic actuator of claim 1, wherein the first handle is spaced a first distance from the first side wall and the second handle is spaced a second distance from the second side wall, the first and second distances being sufficient to allow a user's fingers to fit between the first handle and the first side wall, and the second handle and the second side wall.

6. The external magnetic actuator of claim 1, wherein the second wall is a panel that is coupled to the housing via one or more fasteners.

7. The external magnetic actuator of claim 6, further comprising an adhesive for sealing the panel to the plurality of side walls such that the permanent magnet is hermetically sealed within the actuator body.

8. The external magnetic actuator of claim 1, further comprising first and second sets of projections operable to prevent the first and second walls, respectively, from lying flat against an external surface.

9. The external magnetic actuator of claim 8, wherein the first set of projections include a plurality of projections defining a first distal edge extending beyond a first plane defined by an outside surface of the first wall, the second set of projections include a plurality of projections defining a second distal edge extending beyond a second plane defined by an outside surface of the second wall.

10. The external magnetic actuator of claim 9, wherein the first set of projections extend from the first and second side walls beyond the first wall, and the second set of projections extend from the first and second side walls beyond the second wall.

11. A kit comprising:
- an external magnetic actuator according to any of the preceding claims; and
- a transport container for storing the external magnetic actuator;
- wherein the transport container is operable to contain a magnetic field generated by the permanent magnet of the external magnetic actuator such that a second magnetic field immediately adjacent to the transport container is no greater than 5 milli-Gauss at a distance of 2.1 meters.

* * * * *